United States Patent [19]

Jou et al.

[11] Patent Number: 4,529,712

[45] Date of Patent: Jul. 16, 1985

[54] COATED CELLS AND THEIR USE

[75] Inventors: Yi-Her Jou, Tonawanda; Richard B. Bankert, Amherst, both of N.Y.

[73] Assignee: Research Corporation, New York, N.Y.

[21] Appl. No.: 303,704

[22] Filed: Sep. 18, 1981

[51] Int. Cl.³ .................... A61K 39/00; G01N 33/52
[52] U.S. Cl. .................................................. 436/519
[58] Field of Search ................. 260/112 RB; 436/519

[56] References Cited

U.S. PATENT DOCUMENTS 3,562,385 2/1971 Arquilla ............................. 436/519

Primary Examiner—Christine M. Nucker
Attorney, Agent, or Firm—Scully, Scott, Murphy & Presser

[57] ABSTRACT

Heterobifunctional reagents are used to conjugate molecules or macromolecular structures (e.g., antigens or antibodies) to membranes of non-nucleated or nucleated cells, or to liposomes, these cells being useful in highly sensitive hemolytic or immunocytoadherence assays to detect picogram quantities of antibodies or antigens.

26 Claims, 2 Drawing Figures

COATED CELLS AND THEIR USE

BACKGROUND OF THE INVENTION

Research leading to this invention was sponsored in part by the National Cancer Institute, Grants CA-22786 and CA-25253, by the American Cancer Society, Grant IM-189, and IN-54T-33 as well as the National Institute of Allergy and Infectious Diseases, Grant AI-03962.

1. Field of the Invention

The present invention relates to coated cells or liposomes particularly erythrocytes, and various uses therefor, particularly in the detection of antigens and antibodies employing assays such as the complement-dependent hemolysis and immunocytoadherence techniques.

2. Description of the Prior Art

Erythrocytes (red blood cells) to which protein, polysaccharide or hapten antigens are attached, have been used extensively as target cells to detect antibody in the serum and to quantitate antibody-forming cells and antigen-binding cells at the single cell level (see, for example, Jerne, N. K., et al, Transpl. Rev. 18, 130 (1974); see also, Bartos et al, U.S. Pat. No. 4,239,746; and Molinaro et al, U.S. Pat. No. 4,130,634).

Coated red blood cells have also been particularly useful as target cells in a rapid and sensitive technique for screening numerous samples of hybridoma cell culture fluids for antibody production (Bankert, R. B., et al, Journal of Immunological Methods, 35:23-32 (1980)). In the case of hybridoma derived anti-protein antibodies such a simple screening technique depends upon the availability of a simple and efficient way of attaching proteins to red cell membranes. Ideally, only a very small quantity of protein antigens should be required and the resulting target cells should be stable and capable of reproducibly detecting very small amounts of anti-protein antibody in an immune hemolytic assay.

Various methods have been reported for attaching protein to red blood cells (cf. Boyden, S. V., J. Exp. Med. 93, 107-120 (1951); Pressman, D., et al, J. Immunol. 44:101-105 (1942); Johnson, H. M., et al, ibid, 97:791-796 (1966); Gold, E. R., et al, ibid, 99:859-866 (1967); Golub, E. S., et al, ibid, 100:133-137 (1968); Bankert, R. B., et al, ibid, 123:2466-2474 (1979); Ling, N. R., Immunology 4:49-54 (1961); and Gyenes, L., et al, Immunochemistry 1:43-48 (1964)). However, these methods require substantial amounts of protein (which is often very limited in supply), and may render the cells fragile and susceptible to spontaneous hemolysis.

A need exists for a method of coating cells or celllike structures with substances such as proteins, polysacharides or haptens, which method will allow the cells to retain their viability, not be susceptible to spontaneous lysis, and which method can therefore be used in a variety of applications such as hemolytic assays, cell fusion techniques, and the like.

SUMMARY OF THE INVENTION

It is therefore an object of the invention to provide coated cells which are stable and not susceptible to spontaneous lysis.

It is another object of the invention to provide a method for coating cells by use of a specific group of cross-linking reagents hereinafter described.

It is yet another object of the invention to provide erythrocytes coated with antibodies and/or antigens, which can be used in highly sensitive hemolytic assays, immunocytoadherence assays and other related immunoassays.

Still another object of the invention is to provide a method for assaying antibodies or antigens via a hemolytic or an immunocytoadherence assay procedure, by using the coated erythrocytes or coated viable cells of the invention.

Another object of the invention is to provide a method to selectively label and isolate proteins on the external surface of plasma membranes of eukaryotic cells.

These and other objects of the invention, as will hereinafter become more readily apparent, have been attained by providing:

A conjugate of an animal cell or liposome, especially of a red blood cell, conjugated on the surface thereof via disulfide bonds with one or more molecules or macromolecular structures, wherein said disulfide bonds are derived from a heterobifunctional reagent.

The objects of the invention have also been obtained by providing:

A hemolytic assay method which utilizes red blood cells conjugated to antigens or antibodies to detect antibodies or antigens, using as an improvement the red blood cell conjugates described above.

Another object of the invention has been attained by providing:

A method of stabilizing erythrocytes which comprises reacting the surface of said erythrocytes with an antibody or antigen substituted by the radical of a hetero-bifunctional reagent which can form covalent disulfide bonds with free thiol groups on the surface of said erythrocytes, such as, for example, by reaction with antibody or antigen substituted by a radical derived from N-succinimidyl 3-(2-pyridyldithio)propionate.

BRIEF DESCRIPTION OF THE DRAWINGS

A more complete appreciation of the invention and many of the attendant advantages thereof will be readily obtained as the same becomes better understood by reference to the following detailed description when considered with the accompanying drawings, wherein.

DESCRIPTION OF THE PREFERRED EMBODIMENTS

The present invention is based on the discovery that nuclear or non-nuclear animal cells, or cell-like structures, when covalently coated via disulfide bond formation with a heterobifunctional reagent-modified molecule or macromolecular structure retain their viability (if they are cells), have increased storage stability combared with uncoated cells, and possess a wide range of uses.

By "heterobifunctional" as used in this invention is meant a reagent as defined in Carlsson et al, U.S. Pat. No. 4,232,119 (hereinafter referred to as "Carlsson patent"), and in Carlsson et al, Biochemical Journal 173:23-737 (1978) (hereinafter referred to as "Carlsson paper"). The heterobifunctional reagents defined by the Carlsson patent and paper—both of which are herein incorporated by reference—are low molecular weight (e.g. less than about 1,000) bifunctional reagents carrying at one end of the molecule a functional group which reacts with primary amino groups to give stable amide bonds, and at the other end of the molecule, a functional group which reacts with aliphatic thiols to form disulfides.

The heterobifunctional reagents of the invention can be further defined by the following formula (1):

wherein $R^1$ is 2-pyridyl, 5-nitro-2-pyridyl, or 4-pyridyl; A is an alkyl hydrocarbon residue having 1–10 carbon atoms, preferably 1–6 atoms, and Z is a group of the formula (2):

or acid addition salts of the last mentioned group, wherein n is 2 or 3, and $R^2$ is lower alkyl, preferably methyl or ethyl. Compounds of this formula can be prepared t methods described in the Carlsson patent at columns 5 or 6.

Preferably the heterobifunctional reagent is N-succinimidyl 3-(2-pyridyldithio)propionate, having the following formula (3):

When animal cells, containing reduced thiol groups on their cell surface are reacted with organic or biochemical molecules or macromolecular structures which have been substituted with the heterobifunctional reagents of the invention, it is surprisingly found that the resulting coated cells retain their integrity and viability, and that they are in fact stable at low temperatures (e.g. 4° C.) in saline suspension for longer periods of time than the uncoated cells.

Furthermore, with heterobifunctional reagents, the two reactive groups are directed specifically towards different functional groups (i.e., amino and thiol groups), and one can introduce the thiol-reactive groups into amino-group containing molecules, and then separately couple the substituted molecule to the cell surface via a thiol-disulfide exchange reaction to form disulfide bonds. The high specificity of these two types of reactions result in a highly efficient conjugation of molecule to the cell. On the contrary, prior art intermolecular linking of proteins to cell membranes by means of coupling reagents such as carbodiimide or homobifunctional reagents (e.g., bis-diazotized benzidine or 1,3-difluoro-4,6-dinitrobenzene, in which the two reactive groups are identical), are complicated by intramolecular reactions, cell-cell and molecule-molecule aggregations. Such side reactions obviously decrease the efficiency of coupling the molecules to cell membranes.

The organic or biochemical molecules substituted with the heterobifunctional reagent are useful by themselves as intermediate products for the production of conjugates, and can be stored for indefinite periods until ready for conjugation to cell or cell-like membranes.

By "organic or biochemical molecule or macromolecular structure" is meant any amino group containing molecule or macromolecular structure which is capable of reacting with the amino-reactive end of the heterobifunctional reagent, and which can be coupled to the cells. Among these can be mentioned proteins, amino sugars or amino-lipids, especially antibodies, protein antigens such as enzymes, structural proteins, other cells, small molecules such as amino acids, oligopeptides, carbohydrates, drugs or amino haptens. The resulting substituted molecules or macromolecular structures are bound to the cell by disulfide bond formation in a thiol-disulfide reaction with free thiol groups on the membrane, whereas the conjugated structure is bound to the other end of the heterobifunctional reagent via an amide bond. The resulting composite is insoluble in aqueous media.

The structure of the product conjugate can schematically be represented as follows, (4):

or wherein "Cell" represents a nuclear or non-nuclear animal cell, such as e.g. erythrocytes, myeloma cells, or a cell-derived structure such as a liposome; X represents an organic or biochemical molecule or macromolecular structure as defined supra, and Z is defined as in formula (1), supra.

The conjugation of antibodies and antigens to cells is of particular importance. Among the antibody molecules capable of conjugating to the cells are those of the classes IgG, IgE, IgM, IgA, as well as related molecules such as RF (rheumatoid factor), all of these from either animal sources or tissue culture sources, such as monoclonal antibodies obtained from hybridomas. Other molecules such as protein A from Staphylococcus aureus, can also be used.

The term "antigen" is used broadly in this invention. It encompasses any small molecule, macromolecule, or macromolecular structure capable of being recognized by a corresponding antibody. Among the small molecules are the so-called "haptens" which, although incapable of initiating an immune response when used as challengers by themselves, are capable of being recognized and bound by antibodies, and assayed for in vitro systems. (Immune response with haptens is usually initiated by coupling the hapten to a macromolecular carrier and challenging the host with the resulting coupled product). Among the macromolecules useful as antigens in the present invention are antibodies themselves, other proteins such as enzymes or structural proteins, macromolecular carbohydrates, lipids, nucleic acids, and the like. Among the macromolecular structures useful as antigens in the present invention are viruses or recognizable subfractions thereof, such as rabies virus, hepatitis virus, herpes simplex virus, herpes zoster, hepatitis B surface antigen, and the like. Bacterial antigens can also be coupled to the cells of the invention.

Among the small molecules capable of being conjugated to the cells or cell-like structures of the invention can be mentioned amino acids, carbohydrates, lipids, nucleotides, nucleoside bases, and nucleosides. Pharmacologically and biologically active molecules such as drugs, or prodrugs, can also be coupled to the cells or cell-like structures of the invention.

The animal cells of the invention can comprise both nucleated and non-nucleated cells. Among the nucleated cells of particular interest are myeloma cells, which are used in the preparation of antibody producing hybrids by cell fusion techniques of myeloma cells and lymphocytes. Among the non-nucleated cells of special interest are erythrocytes, particularly sheep red blood cells. Liposomes, or cell membranes from lysed cells can also be used.

The method of coating the cells or cell-like structures with the heterobifunctional reagents of the present invention encompasses two embodiments.

In the first embodiment, the amine-reacting end of the heterobifunctional reagent is first reacted with the amino groups of the appropriate molecule or macromolecular structure to be substituted therewith. The reaction is carried out under the conditions specified by the Carlsson paper, supra. The ratio of the heterobifunctional reagent to amino group containing molecule is preferably 5:1 to 25:1. Once the molecular structure has been coupled to the heterobifunctional reagent via the reaction of the amino groups of the molecule with the amine-reactive end of the heterobifunctional reagent, the resultant thiolreactive conjugate is covalently linked to cell membranes by the reaction of reduced thiol groups on the cell surfaces, with the thiol reacting end of the conjugated heterobifunctional reagent. The ratio of conjugated molecules or macromolecular moieties per single cell is $10^5$–$10^9$ to 1, preferably about $10^6$–$10^8$ to 1, most preferably $10 \times 10^7$ to 1.

In a second embodiment, amino groups on the surface of cells or cell-like structures can be transformed into thiol groups by the use of a thiolating agent such as HS—(CH$_2$)—$_m$C(NH)—OR where R is lower alkyl, m is 1–10; or a reagent such as N-acetylhomocysteinethiohemelactone; or a reagent such as DTDG (dithiodiglycolic acid, HOOC—CH$_2$—SS—CH$_2$—COOH) in the presence of a carbodimide such as 1-ethyl-3-(3-dimethylaminopropyl)carbodiimide (EDCI). For example, DTDG is dissolved in alkaline solution diluted with saline, and the surface amine-containing cells are added at pH 7 in saline at 1–10 mmoles of thiolating agent per $1-10 \times 10^9$ cells. After mixing, the carbodiimide (1–15 mmoles per same number of cells) is added in water, and the preparation is left at about room temperature for 10 min.–2 hr. with stirring so as to keep the cells suspended. After reaction, the cells are washed with saline and stored. Finally, DTDG-coupled cells are treated with a reducing agent such as DTT, as described previously, in order to reduce both the oxidized thiols on the cell surface and the disulfide linkage on the DTDG group, and to release reduced thiols. The reduced thiols are then reacted with the thiol-reacting group of the heterobifunctional reagent, as described previously.

In a particularly preferred embodiment of the present invention, the cells are erythrocytes, the heterobifunctional reagent is N-succinimidyl 3-(2-pyridyldithio)propionate (SPDP), and the structure coupled on the erythrocytes is an antigen or antibody. In this embodiment, the resulting erythrocytes become highly efficient target cells which are stable for several weeks at 4° C. in physiological saline under physiological pH conditions, and are capable of being used in a highly sensitive hemolytic assay without noticeable non-specific lysis, even weeks after the coupling reaction. Because of the high efficiency of the coupling reaction the procedure requires only 10–500 μg of protein for the preparation of target cells that can detect as little as 5 pg of anti-protein antibody in an antibody/complement mediated hemolytic assay.

Figure 1:
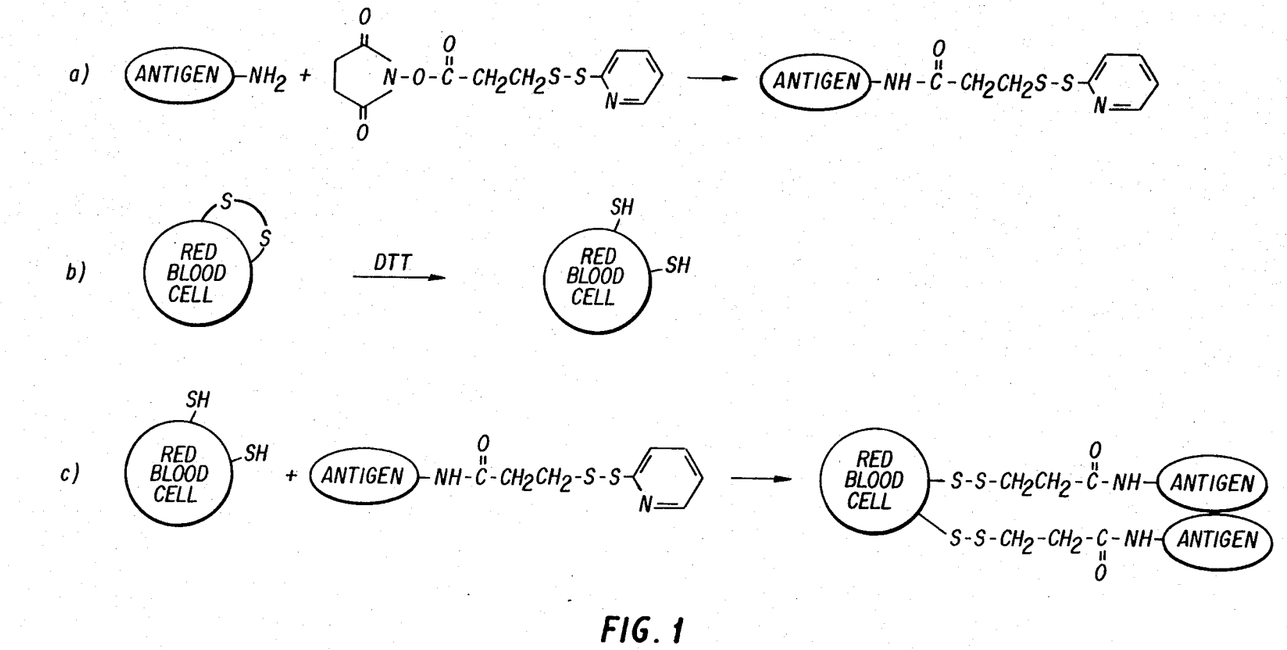
FIG. 1 shows the coupling of protein antigen to red blood cells by (a) Introduction of PDTP groups into a protein antigen by aminolysis; (b) Conversion of the disulfide bonds on the red blood cells into aliphatic thiols by reaction with DTT; and (c) Reaction between the modified protein antigen containing PDTP groups and the reduced red blood cells via thiol-disulfide exchange to form a disulfide-linked protein-red blood cell conjugate.
Figure 2:
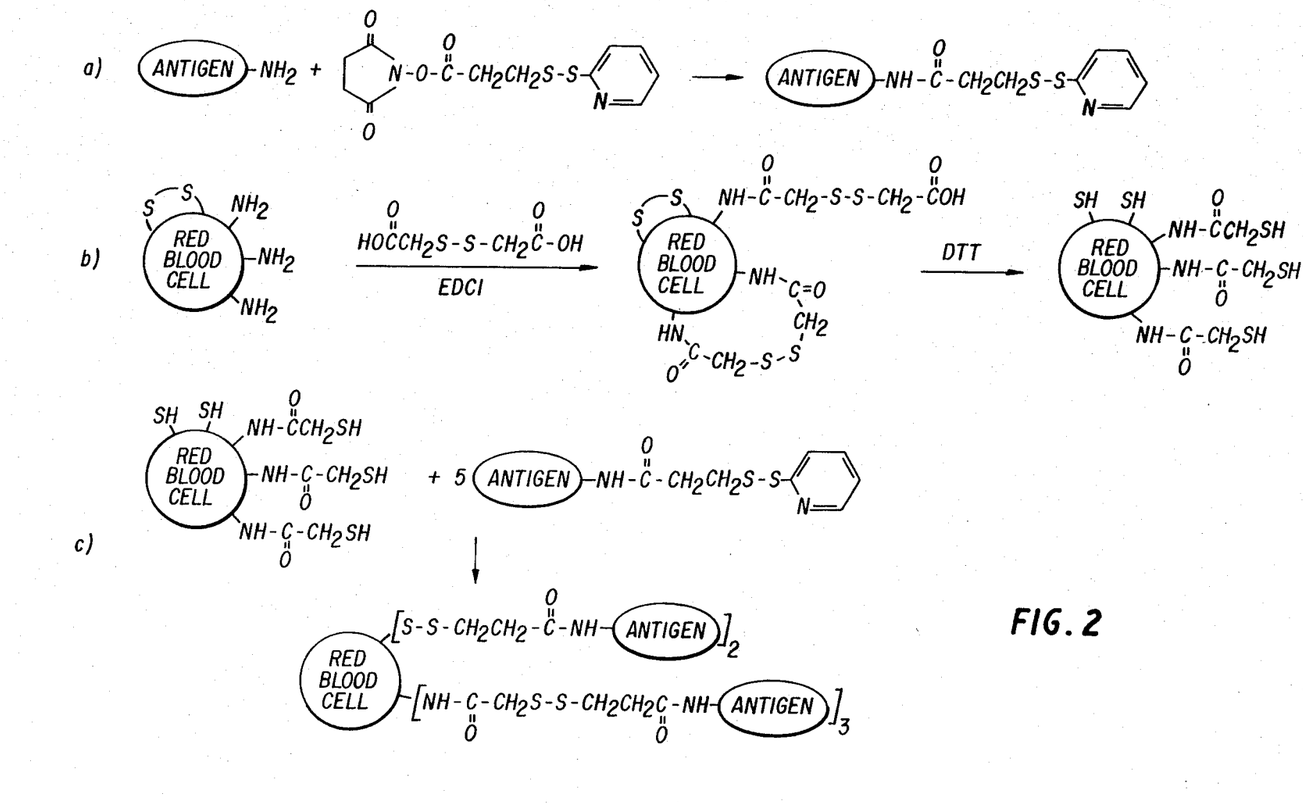
FIG. 2 shows the coupling of protein antigen to sheep red blood cells by (a) Introduction of PDTP groups into a protein antigen by aminolysis; (b) Thiolation of sheep red blood cells by coupling dithiodiglycolic acid (DTDG) to cell membrane protein via EDCI as the condensing agent, followed by conversion of the disulfide bonds on the DTDG coupled sheep red blood cells into aliphatic thiols by reaction with DTT; and (c) Reaction between the modified protein antigen containing PDTP groups and the thiolated sheep red blood cells via thiol-disulfide exchange to form the disulfide linked sheep red blood cell-protein conjugate.

In this specific embodiment, the procedure for preparing the cells generally involves three steps. First, 2-pyridyldithiopropionyl (PDTP) residues are introduced into the protein antigen or antibody by the reaction of a portion of the amino groups of the protein with SPDP. Second, the incorporation of thiol groups to erythrocytes is achieved by coupling DTDG to amino groups on the red cell membrane proteins by using EDCI as the coupling reagent. The disulfide bonds of the DTDG-coupled erythrocytes are then reduced using DTT. Alternatively, of course, the use of DTDG can be voided by simply using DTT to reduce oxidized thiols on the cell surfaces. Thirdly, the PDTP-protein conjugate is covalently coupled to the erythrocytes via thiol-disulfide exchange to form a disulfide-linked protein-erythrocyte conjugate.

In the first reaction (substitution of the aminocontaining antigen or antibody with PDTP groups), the degree of substitution (in moles of PDTP groups per mole of protein) can be varied by using different amounts of reagent. Under controlled experimental conditions, readily ascertainable by those skilled in the art, only a small fraction of the protein amino groups is to be coupled to PDTP groups in order to preserve the structural integrity and antigenicity of the protein. Preferably the number of PDTP group coupled per molecule is no more than 25, most preferably no more than 10. In the third reaction (formation of the protein/cell conjugate) the final molecular ratio of protein to cell is $10^5$–$10^9$ preferably $10^5$–$10^9$:1 most preferably $10 \times 10^7$:1.

Intermolecular linking of antigen to the proteins of the erythrocyte membranes by means of coupling reagents such as EDCI or homobifunctional reagents, such as, for example, bis-diazotized benzidine or 1,3-difluoro-4,6-dinitrobenzene, where the two reactive groups are identical, is complicated by intramolecular reactions on individual protein molecules. Such side-reactions obviously decrease the efficiency of coupling the protein to the erythrocyte membranes. Accordingly, such coupling procedures characteristically require larger quantities of protein for the production of satisfactory target red cells. With the heterobifunctional reagent SPDP, the two reactive groups are directed towards different functional groups, and one can modify the protein to PDTP-protein, which is reactive towards thiol groups, and then separately couple the PDTP-protein to thiol group-containing erythrocytes. Since the thiol-disulfide exchange involved in the coupling of PDTP-protein and thiol-group containing erythrocytes is selective, a highly efficient conjugation of protein and erythrocytes is achieved.

Another advantage of using SPDP as the preferred reagent is that the modification of a protein and the subsequent coupling of a modified protein to thiol-group containing erythrocytes proceed in aqueous media under very mild conditions. Thus, destruction of the antigenic structure of the protein is avoided and the integrity of the erythrocytes is maintained. The antigen-erythrocyte conjugates are found to be stable without significant lysis over a period of at least four weeks of storage at 4° C. in saline. Since DTDG-sheep erythrocytes are also stable in saline at 4° C. for at least four weeks, a large quantity of DTDG-sheep red blood cells can be prepared and stored, thereby facilitating the routine preparation of protein-coupled target cells as needed.

In yet another embodiment of the invention, it is possible to prepare heterobifunctional reagent-coated cells, or cell-like structures which can then be stored and used in subsequent coupling to organic or biochemical molecules or macromolecular structures. In this embodiment, however, the cell membrane is reacted at a free amino group thereon and the organic or biochemical molecule is reacted at a free thiol group thereon. In other words, this embodiment inverts the order and nature of the reaction. For example, an amino containing cell, cell membrane or liposome is first reacted with the heterobifunctional reagent at the amino-reactive end thereof, to yield a cell or cell-like structure coated with a thiol reactive radical derived from the heterobifunctional reagent. A molecule or macromolecular structure containing a free thiol group is then reacted with the coated cell or cell-like structure. The free thiol group on the molecule may either be present originally, or generated by means of a thiolating agent. Preferably, the heterobifunctional reagent is SPDP., The reaction is shown below for an antigen and SPDP, (eg. 5):

If the antigen contains a free amino group, the same can be transformed by means of a thiolating agent such as N-acetylhomocysteinethiolactone into a free SH containing antigen, see supra. Any free —SH groups on the surface of the cell or liposome are first protected or masked with a thiol-protecting group, or alternatively, are first reacted with a homobifunctional disulfide forming reagent e.g. $R'$-S-S-$R'$, (where $R'$ is 2-pyridyl, 5-nitro-2-pyridyl, or 4-pyridyl) (eq. 6):

Once this cell has been further reacted with the heterobifunctional reagent of the invention (e.g., SPDP; eq 7):

the resulting coated cell is reacted with the thiolcontaining antigen, (as in equation (5) supra), at both locations; (eq. 8):

The cells or liposome intermediates e.g., those containing the radical of a heterobifunctional reagent, and useful for further coupling to —SH containing molecules, e.g., "PDTP cell" of equation 5) are also covered by this invention. They can be stored and shipped by themselves or in kits (see infra) for use by the clinical laboratory in situ.

These intermediates can broadly be schematically represented by formula (9):

$$\text{(cell)} - NH - \overset{O}{\underset{\|}{C}} - Z - SS - R^1 \qquad (9)$$

where Z and $R^1$ are defined in formula (1), supra.

The hemolytic assays, and different procedures for carrying out the same, are well known in the art (see, e.g. Stavitsky, Journal of Immunology 74:360, 1954; Bankert, R. B. et al, ibid 123:2466-2474 (1979); Molinaro et al, U.S. Pat. No. 4,130,634, and Bartos et al, U.S. Pat. No. 4,239,746, all herein incorporated by reference).

When an antigen is coupled to an erythrocyte, and the coated erythrocyte is brought into contact with antibody and complement, the antigen coated erythrocytes exhibit certain immunological phenomena, such as agglutination and hemolysis which serve to indicate the presence of the antibody in a substance under test. Inversely, when the red blood cells are coated with antibody, and the coated erythrocytes are brought into contact with an antigen-containing solution or with antigen secreting cells, and with a second antibody plus complement, lysis of the erythrocytes also occurs if free antigen (immunologically complementary to the antibody with which the erythrocytes have been coated) is present in the system.

The existence and extent of lysis of the erythrocytes provide a basis for detecting the presence of antibody or antigen, for determining the concentration thereof, and for ennumerating the cells in the system which secrete the antigen or antibody. Erythrocytes from any animal source such as man, sheep, rabbit or mouse can be used.

For example, in a so-called spot lysis embodiment, the method of the invention involves bringing a material, known or believed to contain in solution a particular antigen or antibody, into contact with red blood cells coated with complementary antibody or antigen. If the antigen or antibody is present in the system, spot lysis of the erythrocytes will occur on treatment first with an antibody or antigen specific for the bound antigen or antibody, and then with an appropriate second antibody plus complement.

Another method is the so-called "radial lysis method", wherein the invention can be used for the quantification of antigen or antibody by single radial immune hemolysis. An antigen or antibody of unknown concentration is allowed to diffuse from a well into a medium such as agar gel, which contains antibody or antigen coated erythrocytes. After a standard period of time, a developer, i.e. an anti-serum containing antibody reactive with the bound antigen (or anti-antibody reactive with the bound antibody), and complement are added, causing localized hemolysis to develop around the well. At low antigen or antibody concentration, the area of the hemolytic circle is proportional to the concentration of the antigen or antibody, which can be determined from standards constructed using known concentrations of antigen or antibody.

Alternatively, in "localized hemolysis", antigen or antibody-mediated lysis of the antibody or antigen coated erythrocytes is used to detect and ennumerate antigen or antibody secreting cells by a plaque-forming cell (PFC) assay.

The spot lysis, radial lysis and localized hemolysis methods are well described in the aforementioned Molinaro et al patent, and no further description will be presented herein.

The method for coupling proteins to red cell membranes described in the present application has made it possible to prepare target cells which can detect extremely small quantities of protein antigens or antibodies under a variety of test conditions. By attaching antibodies, or viral or bacterial antigens to red blood cells, it is possible to detect and identify the presence of either viruses or bacteria, or antibodies to viruses or bacteria. In view of the sensitivity and prolonged stability of the target cells, they can be used as diagnostic reagents with a wide variety of clinical applications.

The ability of such reagents to identify pathogenic viruses or bacteria (in fluids and tissues of humans or animals) in a simple and rapid diagnostic assay renders them highly useful clinically. With the target cells of the present invention, a physician or veterinarian can confirm a presumptive diagnosis of a disease two hours after examining a patient. Such an approach facilitates more definite diagnosis and enables one to initiate earlier therapeutic modalities. Currently, the identification of a virus or a bacteria requires several days, and the commitment of an entire microbiology laboratory.

The target cells can also be applied to the detection of tumor associated antigens. These cells would be useful in the early detection of cancer and in the monitoring of tumor growth.

The coated cells or liposomes can also be used in the so-called immunocytoadherence assay. This assay is useful for the detection of cell-bound antigens or antibodies. It comprises two different cells having a diameter size ratio of at least 2-3:1 and upwards. When one cell type carries antigen (or antibody) on its surface, and the other cell type carries the complementary antibody (or antigen), interaction between them gives rise to cytoadherence, and the formation of "rosettes". Thus the antigen or antibody coated cells or liposomes of the invention can be used to detect cells having complementary antibody or antigen bound thereto.

Another example for use of the target cells is the application to screen serum or blood and plasma for the presence of pathogenic viruses prior to transfusions. The clinical potential of the target cells is accentuated by the fact that they are inexpensive to prepare; all of the chemical reagents are readily available; the assay system in which they are used requires no sophisticated analytical equipment or radioactive tracers as is required for the commonly used radioimmuno-diagnostic assay; and the entire assay can be conducted by one individual with very little training, within two hours after receipt of the sample.

Ihe invention can also be used to facilitate cell-fusion techniques such as those utilized in the preparation of hybridomas. Thus, if a myeloma cell is conjugated via the heterobifunctional reagent with an antigen, and an antigen-specific lymphocyte is then reacted with the antigen coupled myeloma cell, a selective fusion of the lymphocyte with the myeloma results, and yields a higher portion of antigen specific hybridoma, see Bankert, R.B. et al Transpl. Proc. 12:443-446 (1980).

When the cells or liposomes containing drugs, such as, for example, tumor specific drugs, are conjugated to tumor cell recognition structures, such that the coupled cell or liposome can be recognized by tumor cells but not by non-tumor cells, the resulting coupled cell or liposome can work efficiently and selectively as an anti-tumor drug-carrying agent.

When antibodies with well defined specificity (e.g., anti-phthalate antibodies) are conjugated to the free thiol groups on the external surface of the cell membranes by the method described in this invention, the antibody-conjugated, thiol-containing membrane molecules can subsequently be isolated by adsorption on and elution from an immunoadsorbent prepared by coupling antigen (e.g., phthalate) to an insoluble solid phase matrix (e.g., Sepharose ® 4B). The disulfide bonds linking the antibodies and membrane molecules can then easily be split by reduction or by thiol-disulfide exchange as described in Carlsson's paper. Thus the conjugatioin of antibodies to the cell membrane molecules is reversible.

The present invention lends itself readily to the preparation of kits containing individual components to be used in the assay of antigens and/or antibodies. Such a kit would comprise a carrier being compartmentalized to receive in close confinement one or more container means, such as vials.

For example in a first kit embodiment, a first container means may contain appropriate cells, a second vial may contain the structure to be conjugated thereto (such as small molecule, macromolecule or macromolecular structure) already conjugated to the amino-reacting end of the heterobifunctional reagent. When conjugation of the contents of the second vial is desired with the cells of the first vial, a user simply mixes both contents under appropriate reaction conditions. In this embodiment, the kit may also contain one or more control substances to be determined. When the kit is used for a hemolytic assay of a given antigen or antibody, a third vial may be present in the kit containing control amounts of the structure to be determined. Alternatively, a plurality of vials containing different concentrations of the control substance to be determined can be present in the kit.

In a second kit embodiment, one or more container means may contain fully conjugated cells (i.e. cells which have already been reacted with the molecule substituted with heterobifunctional reagent), and may also contain the control substances to be determined in the hemolytic assay.

In a third kit embodiment a first container means may contain cells substituted on the surface thereof with a thiol-reactive radical derived from a heterobifunctional reagent (see formula 9, supra). One or more additional vials may then contain thiol containing molecule or macromolecular structures to be coupled to the reactive cells of the first container means. (If the molecule or macromolecular structure does not have free thiol groups, the same can be generated with thiolating reagents present in additional vials.)

In addition, the kits may also contain vials with appropriate buffers, reducing agents, thiolating agents, carbodiimide coupling agents, thiol activating agents (e.g., 2,2'-dipyridyl disulfide or 4,4' dipyridyl disulfide), and may also contain the necessary instrument means or apparatus means to carry out the hemolytic assay or cytoadherence assays. The kits may also contain additional vials with the required complement, necessary to carry out hemolysis.

Having now generally described this invention, the same will be better understood by reference to certain specific examples which are included herein for purposes of illustration only and are not intended to be limiting unless otherwise specified.

EXAMPLE 1

I. Materials and Methods

Reagents

N-succinimidyl 3-(2-pyridyldithio)propionate (SPDP) is available commercially from Pharmacia Fine Chemicals, Piscataway, N.J. Dithiodiglycolic acid (DTDG), dithiothreitol (DTT) and 1-ethyl-3-(3-dimethylaminopropyl)carbodiimide (EDCI) are available from Aldrich Chemical Co., Milwaukee, Wis. Guinea pig serum, used as a source of complement, is available from GIBCO, Grand Island, New York.

Borate-saline

The borate-saline was prepared by diluting a borate buffer (Pressman, D., et al, Journal of the American Chemical Society, 64:3015-3020 (1942)) (0.167 M $H_3BO_3$, 0.134 M NaCl, 0.022 M NaOH) 12-fold in 0.147 M NaCl followed by adding 1 M HCl to pH 6 or 7.

Antigens

BSA (fraction V powder) and HγG (fraction II) are available commercially from ICN Pharmaceutical, Inc., Cleveland, Ohio. BγG (fraction II) is available from The Sigma Chemical Co., St. Louis, MO. Hy was prepared according to Journal of Cell Biology, 87:137A (1980) following the method described in Citkowitz, E., Developmental Biology, 24:348-362 (1971). PAP was prepared according to Lee, C. L., et al, Cancer Research, 38:2871-2878 (1978). MIgG with anti-phthalate specificity was prepared as reported in Mayers, G. L., et al, Transpl. Proc. 12:413-416 (1980).

Antisera

Rabbit antisera to BSA, BγG and HγG were prepared by injecting each of three rabbits intravenously on three successive weeks, with 10 mg portions of antigen in 1 ml borate-buffered saline. The animals were bled two weeks after the final injection and the sera were processed and stored at −20° C. Rabbit anti-Hy was prepared according to Journal of Cell Biology, 87:137A (1980). Rabbit anti-PAP was prepared by the method of Lee, C. L., Cancer Research 38:2871-2878 (1978). For the preparation of anti-mouse γ-globulin (anti-MγG) antibodies, a rabbit was immunized intramuscularly in multiple sites with 1 mg MIgG in 1 ml of 50 percent complete Freund's adjuvant and was boosted one month later. The animal was bled one week after the last injection. The antiserum was affinity purified by adsorption on and elution from an immunoadsorbent prepared by coupling normal MγG to CNBr-activted Sepharose ®-4B, as described in Cuatrecasas, P., Journal of Biological Chemistry, 245:3059-3065 (1970).

Sheep Red Blood Cells

Sheep red blood cells were obtained weekly by venous puncture of a sheep. The blood was defibrinated as reported in Bankert, R. B., et al, Journal of Immunology, 118:1265-1270 (1977). The red cells were washed three times and made up to 50% (v/v) suspension in pH 7 borate-saline for use in coupling experiments.

Introduction of 3-(2-pyridyldithio)propionyl (PDTP) Groups Into Proteins by SPDP The PDTP groups were introduced into the proteins by reaction with SPDP according to the method reported by the Carlsson paper, supra, and the excess of SPDP reagent was removed by extensive dialysis against PBS (0.075M $KH_2PO_4$, 0.075M NaCl, 0.051M NaOH, pH 7.2). The concentrations and volumes of the different protein solutions and the SPDP reagent used are shown in Table 1.

TABLE 1

| Protein | Concentration of Protein (mg/ml) | Volume of protein solution used in reaction with SPDP (ml) | Volume of SPDP solution used* (ml) | Degree of Substitution Obtained [PDTP]/[Protein]** |
|---|---|---|---|---|
| HγG | 40 | 2 | 0.25 | 1.9 |
| BγG | 40 | 2 | 0.3 | 4.0 |
| BSA | 30 | 2 | 0.25 | 3.2 |
| Hy | 1 | 2 | 0.3 | 8.2 |
| PAP | 12 | 0.5 | 0.05 | 5.6 |
| MIgG | 12 | 0.5 | 0.05 | 11 |

*The 20 mM SPDP solution was freshly prepared in absolute ethanol.
**The molecular weights used for the calculation of molar concentration of proteins are as follows: HγG, 160,000; BγG, 160,000; BSA, 67,000; Hy, 300,000; PAP, 100,000; MIgG, 160,000.

The content of PDTP groups in the modified protein antigens (Ag) (PDTP-Ag) was determined according to the Carlsson paper, supra. Briefly, one ml of a properly diluted PDTP-Ag solution (0.5–1.0 mg/ml) in PBS was treated with 0.1 ml of 1M DTT at room temperature for 40 minutes. This treatment effects the release of pyridine-2-thione, which has a molar absorptivity of $8.08 \times 10^3$ at 343 nm. The amount of pyridine-2-thione released is equivalent to the content of PDTP groups in PDTP-Ag.

Coupling of DTDG to Sheep Red Blood Cells by EDCI

DTDG (182 mg) was dissolved in one ml of 2M NaOH. The DTDG solution was then diluted to 25 ml by adding pH 6 borate-saline. One ml of a 50 percent (v/v) suspension of sheep red blood cells in pH 7 borate-saline was added. After thorough mixing, a freshly prepared solution containing 250 mg of EDCI in 2.5 ml of water was added with mixing. The preparation was left at room temperature for 30 minutes with occasional swirling to keep the red cells suspended. During the course of mixing the reagents, the pH of the reaction mixture rose from 5.3 to 8.4. The cells (DTDG-Sheep Red Blood Cells) were then washed four times with 45 ml portions of PBS, and stored in the same buffer at 4° C. until used.

Reduction of DTDG-Sheep Red Blood Cells to Thioglycolyl-Sheep Red Blood Cells (TG-SRBC) by DTT One-half ml of freshly prepared 1M DTT and 12.5 ml of a 2 percent (v/v) suspension of DTDG-Sheep Red Blood Cells in PBS were mixed in a 15 ml centrifuge tube and stoppered. The reaction was continued at room temperature for one hour on a rotating mixer. The resulting TG-Sheep Red Blood Cells were washed four times with 15 ml portions of PBS and made to a 50 percent (v/v) suspension in preparation for coupling with the PDTP-Ag as described below. Since the thiol group is very reactive and can take part in unwanted reactions, it is recommended that the TG-SRBC be prepared immediately prior to the coupling.

Coupling of PDTP-Ag to TG-SRBC

PDTP-Ag (0.01 mg–2 mg) in PBS (25 μl–200 μl) was mixed with 0.1 ml of a 50 percent (v/v) freshly prepared TG-SRBC suspension on a rotating mixer at room temperature overnight. The resulting protein-coupled cells (Ag-TG-SRBC) were washed three times with 15 ml portions of PBS and a 6% (v/v) suspension prepared for hemolytic assays or for storage at 4° C. until used.

The target cells prepared are described at the left column of Table 2, infra.

Antibody-Complement Mediated Hemolysis

The antibody-complement mediated hemolytic spot test conducted on slides layered with the target cells in agarose (Rowley, D. A., et al, Journal of Experimental Medicine, 120:987–1005 (1964)) was according to the modification by Bankert, et al, Journal of Immunology, 123: 2466–2474 (1979).

Direct Coupling of HγG and BSA to Sheep Red Blood Cells with EDCI

The direct coupling of HγG and BSA to sheep red blood cells with EDCI was according to the procedure of Golub, et al, Journal of Immunology, 100:133–137 (1968).

II. Results

A variety of unrelated proteins were coupled to sheep red blood cells using the heterobifunctional reagents of the invention. These protein-coupled cells were then tested for their ability to detect antibodies of the appropriate specificity. Six different proteins were coupled as examples to sheep red blood cells, resulting in target cells capable of detecting anti-protein antibodies in an immune hemolytic reaction (see Table 2, infra). In addition to testing the immune serum with the appropriate protein-coupled target sheep red blood cells, each undiluted serum was tested for lyses of control sheep red blood cells, i.e., TG-Sheep red blood cells treated the same as the experimental target SRBC, except that the specific protein was omitted from the coupling procedure. No lyses of the control IG-Sheep red blood cells was observed with any of the immune sera.

Table 2 contains the obtained data.

TABLE 2

Antibody-Complement Mediated Hemolysis of Target Cells Prepared by the Coupling of PDTP—Ag to TG—SRBC*

| Target Cell | PDTP—AG reacted with 0.1 ml of 50% (v/v) TG—SRBC (mg/ml) | (ml) | Antibody Preparation** | Hemolytic Titer*** |
|---|---|---|---|---|
| HγG—TG—SRBC | 20 | 0.025 | Rabbit | 64 |
| HγG—TG—SRBC | 20 | 0.1 | anti-HγG antiserum | 128 |

TABLE 2-continued

Antibody-Complement Mediated Hemolysis of Target Cells
Prepared by the Coupling of PDTP—Ag to TG—SRBC*

| Target Cell | PDTP—AG reacted with | | Antibody Preparation** | Hemolytic Titer*** |
|---|---|---|---|---|
| | 0.1 ml of 50% (mg/ml) | (v/v) TG—SRBC (ml) | | |
| BSA—TG—SRBC | 16.5 | 0.025 | Rabbit | 64 |
| BSA—TG—SRBC | 16.5 | 0.1 | anti-BSA antiserum | 64 |
| BγG—TG—SRBC | 10 | 0.025 | Rabbit | 512 |
| BγG—TG—SRBC | 10 | 0.1 | anti-BγG antiserum | 512 |
| Hy—TG—SRBC | 0.4 | 0.025 | Rabbit | 64 |
| Hy—TG—SRBC | 0.4 | 0.1 | anti-Hy antiserum | 128 |
| Hy—TG—SRBC | 0.4 | 0.2 | | 128 |
| PAP—TG—SRBC | 12 | 0.025 | Rabbit | 64 |
| PAP—TG—SRBC | 12 | 0.1 | anti-PAP antiserum | 64 |
| MIgG—TG—SRBC | 11.6 | 0.04 | Affinity purified rabbit anti-MγG antibody | **** |

*All slides were incubated with a goat anti-rabbit immunoglobulin antiserum diluted 1/50 as a facilitator before incubating with guinea pig serum diluted 1/10.
**The rabbit antisera used in this experiment were pre-adsorbed with an equal volume of packed SRBC at 37° C. for one hour. There was no hemolysis of the control TG—SRBC.
***Values in this column indicate the reciprocal of the highest dilution of the antibody preparation that gave an unequivocal positive reaction.
****The quantity of antitody present at the end point is 40 picograms.

Table 2 also contains data comparing the sensitivity of Ag-TG-SRBC prepared with different amounts of PDTP-Ag in detecting anti-protein antibodies. The optimal quantity of PDTP-Ag required for sensitization of TG-SRBC ranged from 10-500 µg in a volume of 0.025-0.04 ml of solution.

In order to determine the sensitivity of Ag-TG-SRBC in terms of the amount of antibody required to produce visible hemolysis, a rabbit anti-MγG was purified via affinity chromatography. It was observed that as little as 40 pg of anti-MγG could be detected via immune hemolysis utilizing MIgG-coupled target SRBC (see Table 2). Less than 500 µg of MIgG was utilized in preparing these target cells.

The efficiency of coupling proteins to sheep red blood cells by the method of the invention and by the EDCI method (Golub, et al, Journal of Immunology, 100:133-137 (1968)) was compared by testing the resulting target cells in an immune hemolytic assay. The data are shown in Table 3.

Finally, experience with one particular protein, i.e. the PAP associated with patients with prostatic cancer, indicates the value of the procedure of the present invention. Here, with as little as 300 µg of PDTP-PAP, it was possible to prepare target cells (PAP-TG-SRBC) which were used successfully to screen hybridoma microcultures for the production of anti-PAP antibodies. In fact, the hemolytic assay utilizing PAP-TG-SRBC permitted the identification of anti-PAP antibody-forming cell hybrids which were not detected by an established radioimmunoassay.

EXAMPLE 2

Erythrocytes such as SRBC may have sufficient free thiol groups and disulfide groups on the cell surface, that after reduction of the latter into thiol groups by treatment with DTT, PDTP-Ag can be conjugated to the cell surface through disulfide bond formation, resulting in antigen-SRBC conjugates suitable for the use as target cells in immunoassays. In order to demonstrate

TABLE 3

Comparison of Ag—TG—SRBC and Ag—SRBC (EDCI)*
in Detecting Antibody-Complement Mediated Hemolysis**

| Target Cells | Quantity of Ag used to Prepare 0.05 ml of Packed Target Cells (mg) | Antiserum*** | Hemolytic Titer**** |
|---|---|---|---|
| HγG—TG—SRBC | 2 | Rabbit anti-HγG | 128 |
| HγG—TG—SRBC | 0.5 | Rabbit anti-HγG | 64 |
| HγG—SRBC (EDCI) | 60 | Rabbit anti-HγG | 64 |
| BSA—TG—SRBC | 1.6 | Rabbit anti-BSA | 64 |
| BSA—TG—SRBC | 0.4 | Rabbit anti-BSA | 32 |
| BSA—SRBC (EDCI) | 240 | Rabbit anti-BSA | 32 |

*Ag—SRBC (EDCI) were prepared ty direct coupling of proteins (HγG and BSA) to SRBC by EDCI according to the method of Golub, et al.
**All slides were incubated with a goat anti-rabbit immunoglobulin antiserum diluted 1/50 as a facilitator before incubating with guinea pig serum diluted 1/10.
***The rabbit antisera were pre-adsorbed with an equal volume of packed SRBC at 37° C. for one hour. There was no hemolysis of the control TG—SRBC.
****Values of this column indicate the reciprocal of the highest dilution of antiserum that gave an unequivocal positive reaction.

It is significant that in order to achieve the same sensitivity (hemolytic titer), the quantity of antigen required for the Ag-TG-SRBC preparation of the invention is 120-600 times less than that required using EDCI coupling.

this, BSA-SS-SRBC and MIgG-SS-SRBC were prepared and tested in a hemolysis assay as described in the following.

Half a ml of bovine serum albumin (BSA) (15 mg/ml in PBS), and affinity purified monoclonal mouse IgG (12 mg/ml in PBS) with specificity for phthalate, were each treated with 0.05 ml of 20 mM SPDP in absolute alcohol according to the procedures described previously. The molar ratio of PDTP groups and protein determined in the manner as described supra) is 3.2 for PDTP-BSA and 11 for PDTP-mouse IgG.

Sheep red blood cells were reduced by DTT by taking one-half ml of freshly prepared 1M DTT and 12.5 ml of a 2% suspension of red blood cells in PBS, and mixed in a 15 ml centrifuge tube and stoppered. The reaction was continued at room temperature for 1 hr. on a rotating mixer. The resulting reduced red blood cells were washed four times with 15 ml portions of PBS.

One-tenth ml of PDTP-BSA (3 mg/ml) and 0.1 ml of PDTP-MIgG (0.2 mg/ml) in PBS were each treated with 0.05 ml of DTT-reduced sheep red blood cells according to the procedures described previously.

In an antibody complement mediated hemolytic assay, the target cells, BSA-SS-SRBC were shown to be lysed by rabbit anti-BSA anti-serum diluted 1:64, and MIgG-SS-SRBC by affinity purified rabbit anti-MIgG at the concentration of 5 ng/ml. All slides were incubated with a goat anti-rabbit immunoglobin anti-serum diluted 1:100 as a facilitator before incubating with ginnea pig serum diluted 1:10. The rabbit anti-BSA anti-serum was preadsorbed with an equal volume of packed sheep red blood cells at 37° C. for 1 hr. The control target cells (DTT-reduced sheep red blood cells) were not lysed by SRBC adsorbed anti-BSA anti-serum or affinity purified rabbit anti-MIgG antibodies.

EXAMPLE 3

Labeling of Nucleated Cell Surface Proteins with Monoclonal Antibodies

Ten mg of monoclonal anti-phthalate antibody in 1 ml of PBS prepared as reported in Mayers, G. L. et al., (Transpl. Proc. 12:413–416, 1980) was treated with 100 $\mu$l of 20 mM SPDP in absolute alcohol according to the method reported by the Carlsson paper, supra, and the excess of SPDP reagent was removed by extensive dialysis against PBS.

A portion ($\sim 10^8$ cells) of X63-Ag8 6.53 murine myeloma cells were washed three times with 10 ml portion of PBS. To a pellet of $10^7$ cells in a centrifuge tube was added 25 $\mu$g of the SPDP modified monoclonal anti-phthalate antibody. The cells were incubated at 37° C. for one hour on a shaker, washed three times with 1 ml portion of PBS and then suspended to a concentration of $\sim 1 \times 10^6$ cell/ml in Dulbecco's modified Eagle's medium.

The successful coupling of the monoclonal antibodies to the cell membrane and the preservation of the antigen combining site was established by an immunocytoadherence assay. In this assay, the antibody-coupled cells are tested for their ability to bind sheep red blood cells coupled with phthalate prepared as reported in Jou, Y-H. et al. (J. Immunol. Methods 42:79–92, 1981). Successful coupling of antibodies results in the adherence of phthalate-coupled sheep red blood cells to the surface of the antibody-coupled myeloma cells forming what are referred to as rosettes.

Following the completion of the immunocytoadherence assay, the cells were examined microscopically and all (100 percent) of the nucleated cells were found to form rosettes with the phthalate-coupled sheep red blood cells while none of the control nucleated cells (which were not treated with SPDP modified antibody) formed rosettes with the indicating red cells. The nucleated cells were incubated at 37° C. following the coupling of anti-phthalate antibodies and then tested in the immunocytoadherence assay after various periods of time. It was found that the cell surface coupled antibodies were completely cleared after 20 hour of incubation at 37° C. as indicated by the disappearance of rosette-forming cells. Furthermore, after the coupling reaction the antibody-coupled nucleated cells were found to retain the same viability of the control nucleated cells which were treated the same except that buffer instead of SPDP-modified antibody was used in the coupling reaction.

The anti-phthalate antibody conjugated cell membrane molecules can be easily isolated by passing the membrane preparation of the anti-phthalate antibody labeled cells through an affinity column packed with immunoadsorbents, i.e., phthalate-coupled Sepharose ® 4B, followed by eluting with 0.5M phthalate, pH 8.

The disulfide bonds linking the cell membrane molecules and anti-phthalate antibodies can be specifically cleaved by reduction with DTT according to the method reported in Carlsson paper, supra.

Having now fully described this invention it will be understood by those skilled in the art that the same can be practiced within a broad range of equivalent concentrations, proportions, and other such parameters, without affecting the spirit or scope of the invention or of any embodiments thereof.

What is claimed as new and intended to be covered by Letters Patent of the United States is:

1. A conjugate of an animal cell comprising an amino group containing molecule or macromolecular structure connected via an amide bond to the amino-reactive end of a heterobifunctional cross-linking reagent, the thiol-reactive end of said connected reagent being linked via a disulfide bond to an animal cell whose surface contains thiol groups.

2. The conjugate of claim 1 wherein the cell carries on its surface one or more radicals of the formula wherein
A is $C_1$-$C_{10}$ alkyl group;
Y is O or NH; and
X is said molecule or macromolecular structure.

3. The conjugate of claim 2 which is derived from a red blood cell.

4. The conjugate of any of claims 2 or 3 wherein said radical has the formula

5. The conjugates of any of claims 2 or 3 which are bonded to said radicals via thiol groups on the surface of said cells; or by thiol groups derived from amino groups on the surface of said cells, which amino groups are converted into thiol group-containing amides.

6. The conjugate of claim 1 wherein said heterobifunctional reagent has the formula wherein R¹ is selected from the group consisting of 2-pyridyl, 4-pyridyl and 5-nitro-2-pyridyl, and Z is selected from the group consisting of acid addition salts of wherein n is 2 or 3, and R² is lower alkyl.

7. The conjugate of claim 1 wherein said aminogroup containing molecule or macromolecular structure is selected from the group consisting of an antibody, an antigen, a hapten and a cell.

8. The conjugate of claim 7 wherein said aminogroup containing molecule or macromolecular structure is an antigen selected from the group consisting of a virus, a bacterium, and a protein.

9. The conjugate of claim 1 wherein the ratio of units of molecule or macromolecular structure to single cell is $10^5$–$10^9$:1.

10. The conjugate of claim 1 wherein said cell is a nucleated cell.

11. An animal cell substituted on one or more amino groups on the surface thereof with a radical of the formula:

wherein
A is a $C_1$–$C_{10}$ alkyl group and
R¹ is selected from the group consisting of 2-pyridyl, 4-pyridyl and 5-nitro-2-pyridyl.

12. The cell of claim 11 wherein said radical has the formula

13. The cell of claim 12 wherein said radical has the formula

14. The cell of claim 11 which is nucleated or non-nucleated.

15. The cell of claim 11 which is a red blood cell.

16. The cell of claim 11 which also carries on said surface thiol groups bonded to a radical of the formula —S—R'.

17. A process of conjugating a thiol-containing molecule or macromolecular structure to an animal cell which comprises reacting the cell of any of claims 11 or 16 with said thiol-containing molecule or macromolecular structure.

18. A process of conjugating an amino group containing molecule or macromolecular structure to an animal cell which comprises:
reacting said amino group on said molecule or macromolecular structure with a heterobifunctional reagent of the formula:

wherein R¹ is selected from the group consisting of 2-pyridyl, 4-pyridyl and 5-nitro-2-pyridyl, A is a $C_1$–$C_{10}$ alkyl and Z is selected from the group consisting of and acid addition salts of wherein n is 2 or 3, and R² is lower alkyl, thereby forming an amide of the formula (1)

wherein X represents said molecule or macromolecular structure; then
reacting a thiol group containing animal cell with said amide of formula (1).

19. The process of claim 18 wherein said molecule or macromolecular structure is selected from the group consisting of a peptide, an amino acid, an amino sugar, and a cell.

20. The process of claim 19 wherein said molecule or macromolecular structure is an antibody or an antigen.

21. The process of claim 18 wherein said animal cell is a nucleated cell or a non-nucleated cell.

22. The process of claim 18 wherein said cell is a red blood cell.

23. The process of claim 18 wherein said thiol group containing animal cell is prepared by treating said animal cell with a disulfide reducing agent.

24. The process of claim 18 wherein said thiol group containing animal cell is prepared by transforming amino groups of an amino-group containing cell, to thiol containing-amide groups.

25. The process of claim 24 wherein said transformation is carried out by reacting said amino group of said cell with dithiodiglycolic acid, and reducing the resulting dithiodiglycolyl amide with a disulfide reducing agent.

26. A conjugate of an animal cell comprising an thiogroup containing molecule or macromolecular structure connected via a disulfide bond to the thio-reactive end of a heterobifunctional cross-linking reagent, the amino-reactive end of said cross-linking reagent being linked via an amide bond to an animal cell whose surface contains amino groups.

* * * * *